(12) United States Patent
Radomsky et al.

(10) Patent No.: US 6,247,329 B1
(45) Date of Patent: Jun. 19, 2001

(54) THERMAL ENVELOPE

(75) Inventors: Ronen Radomsky, Romema Haifa; Baruch Gorlovitsky, Nesher; Shai Amisar, Jerusalem, all of (IL)

(73) Assignee: Thermal Clinical Solutions Ltd., Tortola (VG)

( * ) Notice: Subject to any disclaimer, the term of this patent is extended or adjusted under 35 U.S.C. 154(b) by 0 days.

(21) Appl. No.: 09/529,620
(22) PCT Filed: Oct. 11, 1998
(86) PCT No.: PCT/IL98/00492
§ 371 Date: Apr. 13, 2000
§ 102(e) Date: Apr. 13, 2000
(87) PCT Pub. No.: WO99/19652
PCT Pub. Date: Apr. 22, 1999

(30) Foreign Application Priority Data

Oct. 13, 1997 (IL) .............................................. 121960

(51) Int. Cl.$^7$ .................................................. F25D 3/08
(52) U.S. Cl. .............................................. 62/457.2; 62/371
(58) Field of Search .................................. 62/457.2, 371, 62/530

(56) References Cited

U.S. PATENT DOCUMENTS

| | | | |
|---|---|---|---|
| 5,022,521 | * 6/1991 | Kane | 206/370 |
| 5,069,208 | 12/1991 | Noppel et al. | |
| 5,361,603 | * 11/1994 | Merritt-Munson | 62/457.2 |
| 5,840,080 | 11/1998 | Der Ovanesian | |
| 5,865,314 | 2/1999 | Jacober | |

FOREIGN PATENT DOCUMENTS

1495366 * 12/1977 (GB) ...................................... 62/530

* cited by examiner

*Primary Examiner*—William Doerrler
*Assistant Examiner*—Melvin Jones
(74) *Attorney, Agent, or Firm*—Darby & Darby

(57) ABSTRACT

This invention discloses a thermal envelope including a pouch (12) and a flap that closes the pouch and thermal capacitance material (18) that lines the pouch, wherein the thermal capacitance material (18) has an initial temperature in a temperature range of −5 degrees C. to 20 degrees C., characterized by the thermal capacitance material having a thermal that maintains a temperature of the medical sample placed in the pouch (12) within the temperature range during a period of time not more than 7 hours from the time the medical sample was placed in the pouch. A method for sending a medical sample from a sampling site to a laboratory is also disclosed.

11 Claims, 1 Drawing Sheet

THERMAL ENVELOPE

FIELD OF THE INVENTION

The present invention relates generally to thermally insulating envelopes and particularly to an envelope which cools or heats medical samples placed therein and maintains a temperature thereof for a predetermined period of time.

BACKGROUND OF THE INVENTION

Medical samples, such as blood, urine or other exudates, are often taken from a patient at a clinic or doctor's office and then sent to a laboratory elsewhere for analysis. The sample is sometimes chilled or even frozen before being sent for analysis. Other times it is imperative to maintain the sample at room temperature. Thus it is desirable to maintain the temperature of the sample, be it room or sub-room temperature, while in transit to the laboratory until the time of analysis.

Although many insulating devices are well known, ranging from insulated boxes to insulated flasks, it is desirable to provide an inexpensive device for maintaining the temperature of medical samples for a predetermined period of time.

SUMMARY OF THE INVENTION

The present invention seeks to provide an improved envelope which cools or heats medical samples placed therein and maintains a temperature thereof for a predetermined period of time. Specifically the present invention provides a novel method for sending a medical sample, such as a blood sample, from a sampling site to a laboratory for analysis thereof. The invention may be particularly useful for sending samples from one location in a hospital to another.

The envelope of the present invention preferably has an inner lining of an insulating material and another inner lining of a freezable material. The envelope is precooled to a temperature typically in the range of −5° C. to 20° C. Alternatively the envelope may be pre-heated if it is desired to maintain the sample at a warm temperature. The medical sample is then simply placed in the envelope and sent to the laboratory. The envelope of the present invention differs from the prior art in that it is designed to maintain the temperature of the sample in the abovementioned temperature range for only a short period of time, such as from 0.5–7 hours. This eliminates the need for expensive insulating devices which are an "over-kill" solution, and provides a simple and inexpensive solution to the problem of sending the sample to the laboratory while maintaining the desired temperature.

There is thus provided in accordance with a preferred embodiment of the present invention a thermal envelope including a pouch and a flap that closes the pouch, and a thermal capacitance material that lines the pouch, wherein the thermal capacitance material has an initial temperature in a temperature range of −5° C. to 20° C., characterized by the thermal capacitance material having a thermal capacitance that maintains a temperature of the medical sample placed in the pouch within the temperature range during a period of time not more than 7 hours from the time the medical sample was placed in the pouch.

Alternatively the insulating material maintains the temperature of the medical sample within the temperature range during a period of time not more than 0.5–7 hours from the time the medical sample was placed in the pouch.

In accordance with a preferred embodiment of the present invention the thermal envelope also includes a liner of an insulating material between the thermal capacitance material and an inner surface of the pouch.

Further in accordance with a preferred embodiment of the present invention the thermal capacitance material is selected from the group consisting of water, a gel having a high water content, a polyvinyl alcohol, and a water-soluble organic compound. Preferably the thermal capacitance material is freezable and the envelope is heatable in a microwave oven.

There is also provided in accordance with a preferred embodiment of the present invention a method for sending a medical sample from a sampling site to a laboratory including maintaining a thermal envelope, at a predetermined temperature range different from room temperature, the thermal envelope having a pouch and a flap that closes the pouch, placing a medical sample in the thermal envelope, the envelope maintaining the sample within the temperature range for a predetermined time; and sending the sample to a laboratory. The sample may be maintained in a temperature range of −5° C. to 20° C., for example, or 40° C. to 50° C., as another example.

BRIEF DESCRIPTION OF THE DRAWINGS

The present invention will be understood and appreciated more fully from the following detailed description, taken in conjunction with the drawing in which.

DETAILED DESCRIPTION OF A PREFERRED EMBODIMENT

Figure 1:
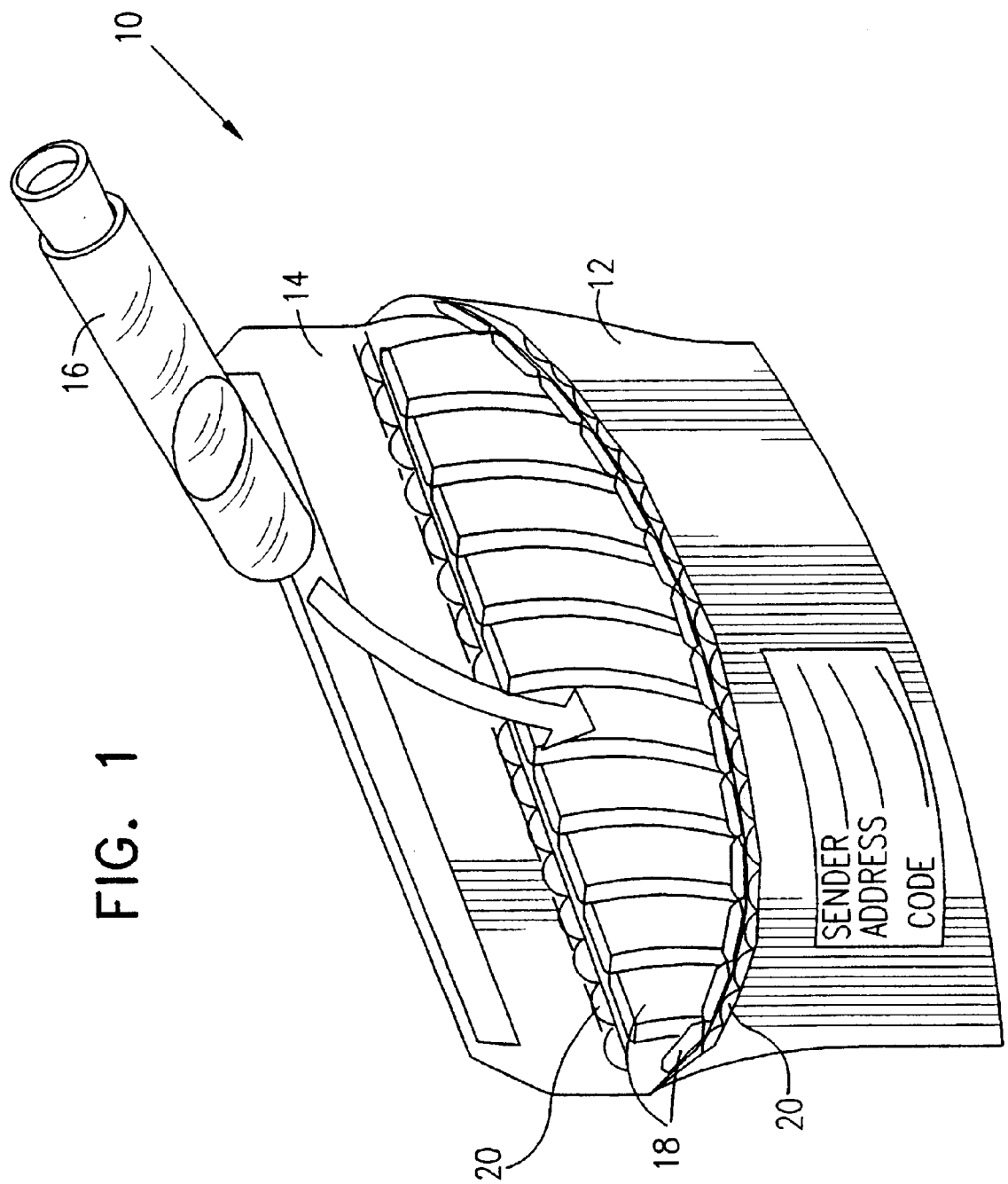
FIG. 1 is a simplified pictorial illustration of a thermal envelope constructed and operative in accordance with a preferred embodiment of the present invention.

Reference is now made to FIG. 1 which illustrates a thermal envelope 10 constructed and operative in accordance with a preferred embodiment of the present invention. Insulating envelope 10 includes a pouch 12 and a flap 14 that closes pouch 12, preferably any type of glueable flap used with conventional envelopes. Insulating envelope 10 is preferably constructed of materials heatable in a microwave oven. Pouch 12 is adapted for placing therein a medical sample 16, such as blood.

Pouch 12 has an inner liner of a thermal capacitance material 18. Thermal capacitance material 18 may be selected from a variety of materials, for example, but not limited to, water, a gel having a high water content, a polyvinyl alcohol, and a watersoluble organic compound. Thermal capacitance material 18 may be packaged in plastic capsules, as shown in FIG. 1.

A liner of an insulating material 20, such as plastic bubble material or polystyrene foam, for example, is preferably disposed between thermal capacitance material 18 and an inner surface of pouch 12.

Envelope 10 is preferably stored in a refrigerator or freezer and maintained in a temperature range of typically, but not necessarily, −5° C. to 20° C. Alternatively, envelope 10 may be pre-heated and maintained in a temperature range of typically, but not necessarily, 40–50° C. Thermal capacitance material 18 has a thermal capacitance and insulating material 20 has a thermal resistance such that the temperature of medical sample 16 is maintained within the abovementioned temperature range during a predetermined period of time from when medical sample 16 was placed in pouch 12. For example, materials 18 and 20 may be selected to maintain the temperature of medical sample 16 in the range of −5 ° C. to 20° C. (or 40–50° C.) during a period of time not more than 7 hours from the time medical sample 16 was placed in pouch 12. Alternatively, the period of time of maintaining the temperature may range from 0.5–7 hours.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A thermal envelope comprising:

a pouch and a flap that closes said pouch; and a thermal capacitance material that lines said pouch, wherein said thermal capacitance material has an initial temperature in a temperature range of −5° C. to 20° C., characterized by said thermal capacitance material having a thermal capacitance that maintains a temperature of said medical sample placed in said pouch within said temperature range during a period of time not more than 7 hours from the time said medical sample was placed in said pouch.

2. The thermal envelope according to claim 1 and wherein said thermal capacitance material maintains the temperature of said medical sample within said temperature range during a period of time not more than 2 hours from the time said medical sample was placed in said pouch.

3. The thermal envelope according to claim 1 and wherein said thermal capacitance material maintains the temperature of said medical sample within said temperature range during a period of time not more than 1 hour from the time said medical sample was placed in said pouch.

4. The thermal envelope according to claim 1 and wherein said thermal capacitance material maintains the temperature of said medical sample within said temperature range during a period of time not more than 1.5 hours from the time said medical sample was placed in said pouch.

5. The thermal envelope according to claim 1 and comprising a liner of an insulating material between said thermal capacitance material and an inner surface of said pouch.

6. The thermal envelope according to claim 1 and wherein said thermal capacitance material is selected from the group consisting of water, a gel having a high water content, a polyvinyl alcohol, and a water-soluble organic compound.

7. The thermal envelope according to claim 1 and wherein said thermal capacitance material is freezable.

8. The thermal envelope according to claim 1 and wherein said envelope is heatable in a microwave oven.

9. A method for sending a medical sample from a sampling site to a laboratory, comprising:

maintaining a thermal envelope, at a predetermined temperature range different from room temperature, said thermal envelope having a pouch and a flap that closes said pouch;

placing a medical sample in said thermal envelope, said envelope maintaining said sample within said temperature range for a predetermined time; and sending the sample to a laboratory.

10. A method according to claim 9 and comprising maintaining said envelope in a temperature range of −5° C. to 20° C.

11. A method according to claim 9 and comprising maintaining said envelope in a temperature range of 40° C. to 50° C.

* * * * *